(12) United States Patent
Spring et al.

(10) Patent No.: US 11,762,186 B2
(45) Date of Patent: Sep. 19, 2023

(54) INVESTIGATION INSTRUMENT

(71) Applicant: Scholly Fiberoptic GmbH, Denzlingen (DE)

(72) Inventors: Patrick Spring, Freiburg (DE); Johannes Bourbon, Freiburg (DE); Alexander Kohler, Freiburg (DE); Matthias Kuhn, Freiburg (DE)

(73) Assignee: Scholly Fiberoptic GmbH, Denzlingen (DE)

( * ) Notice: Subject to any disclaimer, the term of this patent is extended or adjusted under 35 U.S.C. 154(b) by 0 days.

(21) Appl. No.: 16/706,053

(22) Filed: Dec. 6, 2019

(65) Prior Publication Data
US 2020/0192078 A1 Jun. 18, 2020

(30) Foreign Application Priority Data
Dec. 17, 2018 (DE) .................. 102018132449.9

(51) Int. Cl.
*H05K 1/02* (2006.01)
*H05K 1/11* (2006.01)
(Continued)

(52) U.S. Cl.
CPC ......... *G02B 23/2484* (2013.01); *H04N 23/54* (2023.01); *H05K 1/028* (2013.01); *H05K 1/0298* (2013.01); *H04N 23/555* (2023.01); *H05K 2201/10151* (2013.01); *H05K 2201/10734* (2013.01)

(58) Field of Classification Search
CPC ............ H05K 1/02; H05K 1/18; H05K 1/028; H05K 1/0298; H05K 1/11; H04N 5/225; H04N 5/228; H04N 5/235; H04N 5/374; H04N 5/2253; H04N 7/18; G02B 23/24; G02B 23/2484; G02B 7/02; G02B 7/04; A61B 1/00; A61B 1/04; A61B 1/05; H01R 12/59; H01R 12/67; H01L 27/146
USPC ...... 361/749; 600/109, 110, 167; 250/208.1; 348/76, 208.5, 357, 373, 374, 375; 359/557, 811, 896
See application file for complete search history.

(56) References Cited

U.S. PATENT DOCUMENTS 4,878,485 A * 11/1989 Adair ................. A61B 1/00101
600/122
5,748,448 A * 5/1998 Hokari ............... H01L 31/0203
174/541

(Continued)

FOREIGN PATENT DOCUMENTS

DE 102015204884 7/2016
JP 2010263020 11/2010

*Primary Examiner* — Xiaoliang Chen
(74) *Attorney, Agent, or Firm* — Volpe Koenig

(57) ABSTRACT

For the miniaturization of an investigation instrument (1), which includes a sensor (3), which is arranged in the interior of a long shaft (2) and is electrically contact-connected by a connection (8), it is provided that a flexible bending section (10) is configured on the connection (8), and is thus connected with a contact-connection section (9), which is contact-connected with contacts (4) of the sensor (3) on the reverse side such that, firstly, the entire connection (8) is arranged in the shadow of the image sensor (3) and, secondly, the bending section (10) originates from the contact-connection section (9) within a field (5) which is subtended by the reverse-side contacts (4) of the sensor (3).

19 Claims, 4 Drawing Sheets

(51) Int. Cl.
*H05K 1/18* (2006.01)
*H04N 5/225* (2006.01)
*H04N 5/228* (2006.01)
*H04N 5/235* (2006.01)
*H04N 5/374* (2011.01)
*H04N 7/18* (2006.01)
*G02B 23/24* (2006.01)
*G02B 7/02* (2021.01)
*G02B 7/04* (2021.01)
*A61B 1/00* (2006.01)
*A61B 1/04* (2006.01)
*A61B 1/05* (2006.01)
*H01R 12/59* (2011.01)
*H01R 12/67* (2011.01)
*H01L 27/146* (2006.01)
*H04N 23/54* (2023.01)
*H04N 23/50* (2023.01)

(56) References Cited

U.S. PATENT DOCUMENTS

| | | | | |
|---|---|---|---|---|
| 6,002,437 | A * | 12/1999 | Morioka | H04N 5/2252 348/373 |
| 9,929,483 | B2 | 3/2018 | Wieters et al. | |
| 10,524,643 | B2 * | 1/2020 | Birnkrant | G01J 1/0477 |
| 2004/0130640 | A1 * | 7/2004 | Fujimori | H01L 31/0203 348/294 |
| 2006/0055787 | A1 * | 3/2006 | Hirota | H04N 5/2253 348/208.5 |
| 2008/0058601 | A1 * | 3/2008 | Fujimori | A61B 1/041 600/167 |
| 2009/0084191 | A1 * | 4/2009 | Matsui | G01L 19/0645 29/592.1 |
| 2010/0091120 | A1 * | 4/2010 | Nagata | H04N 5/23287 348/208.4 |
| 2011/0118549 | A1 * | 5/2011 | Han | A61B 1/04 600/109 |
| 2011/0141584 | A1 * | 6/2011 | Henderson | H02N 2/22 359/811 |
| 2011/0249106 | A1 * | 10/2011 | Makino | H05K 1/189 348/76 |
| 2011/0262121 | A1 * | 10/2011 | Yanagisawa | H04N 5/23287 396/55 |
| 2013/0119785 | A1 * | 5/2013 | Han | G02B 7/102 310/12.16 |
| 2014/0184891 | A1 * | 7/2014 | Lee | H04N 5/2253 348/357 |
| 2014/0371530 | A1 * | 12/2014 | Wieters | A61B 1/00114 600/109 |
| 2015/0228678 | A1 * | 8/2015 | Yoshida | A61B 1/05 600/110 |
| 2015/0264290 | A1 * | 9/2015 | Happoya | H04N 5/2254 348/373 |
| 2015/0378144 | A1 * | 12/2015 | Han | G02B 23/2484 250/208.1 |
| 2016/0205296 | A1 * | 7/2016 | Igarashi | A61B 1/051 348/76 |
| 2016/0209637 | A1 * | 7/2016 | Fujimori | H04N 5/374 |
| 2016/0338579 | A1 * | 11/2016 | Amano | A61B 1/005 |
| 2017/0108692 | A1 * | 4/2017 | Kitano | G02B 23/2484 |
| 2017/0164820 | A1 * | 6/2017 | Segawa | A61B 1/0011 |
| 2017/0317413 | A1 * | 11/2017 | Mei | H01Q 1/48 |
| 2018/0006389 | A1 * | 1/2018 | Wieters | H01R 12/67 |
| 2018/0324338 | A1 * | 11/2018 | Chung | H04N 5/2254 |
| 2018/0329277 | A1 * | 11/2018 | Han | G03B 13/36 |
| 2018/0343743 | A1 * | 11/2018 | Qiu | G06F 1/1658 |
| 2019/0133423 | A1 * | 5/2019 | Birnkrant | A61B 1/051 |
| 2019/0150711 | A1 * | 5/2019 | Chiu | A61B 1/0684 |

* cited by examiner

INVESTIGATION INSTRUMENT

INCORPORATION BY REFERENCE

The following documents are incorporated herein by reference as if fully set forth: German Patent Application No. 10 2018 132 449.9, filed Dec. 17, 2018.

BACKGROUND

The invention relates to an investigation instrument having a shaft, in which a sensor is arranged which, by reverse-side electrical contacts, which subtend a field on the reverse side of the sensor, is electrically contact-connected by a connection.

Instruments of this type are known, for example, from the field of endoscopy, where very small image sensors, which are arranged at the distal end of an endoscope shaft, are connected in this manner to a circuit board by way of connection, in order to permit the relaying of signals from the image sensor to the proximal end of the shaft. In many cases, to this end, the circuit board incorporates a planar region for the electrical contact-connection of the sensor, which thus constitutes a contact-connection section, and a bending section, in which electrical connection lines are routed out from the contact-connection section of the circuit board. Arrangements of this type are disadvantageous, in that the circuit board, specifically the flexible bending section thereof, dictates a larger dimension transversely to the shaft direction than is strictly necessary for the arrangement of the sensor.

In other endoscopes which are known from the prior art, the image sensor is fitted to the upper side or underside of a rigid circuit board, wherein the circuit board, and thus the sensor, is arranged in a longitudinal plane of the endoscope shaft. Structural space transversely to the shaft direction can thus be economized, as image sensors typically assume only a limited height, in comparison with their outline dimensions. However, the viewing direction of the sensor is then oriented orthogonally to the plane of the circuit board, and thus orthogonally to the longitudinal axis of the endoscope. Customarily, however, it is intended that the viewing direction of the endoscope should be oriented in the direction of the longitudinal axis, or in any event at only a small angle to the longitudinal axis. Consequently, in configurations of this type, it is generally necessary to employ a prism or a mirror in order to rotate the viewing direction of the sensor, thereby increasing the complexity of the endoscope.

The alternative employment of individual cables by way of connection for the electrical contact-connection of the sensor is also disadvantageous, as this procedure is associated with a high complexity of assembly which, moreover, provides only a limited facility for automation, thereby resulting in high production costs.

SUMMARY

The object of the invention is the achievement of a further miniaturization of investigation instruments of the above-mentioned type, and simultaneously to permit a simple manufacture and assembly of the investigation instrument. To this end, an innovative installation and connection technique is intended to be provided for the connection of instrument sensors, which dispenses with plug connectors and is nevertheless reliable.

For the fulfilment of this object, according to the invention, an investigation instrument having one or more characteristics of described below is provided. Specifically, for the fulfilment of the object according to the invention, in an investigation instrument of the above-mentioned type, it is provided that the connection comprises a flat contact-connection section for the contact-connection of the contacts, and a flexible bending section, in which electrical connection lines are brought out of the contact-connection section from the rear of the sensor, wherein the bending section is arranged within a shadow which is cast by the field along a longitudinal axis of the shaft. The shadow region can thus be characterized, for example, in that the bending section lies within a shadow which is defined by a field which subtends a rearward extension of the viewing direction in a notional optically non-transparent body, and/or within a shadow which is defined by a field which subtends an extension along the longitudinal axis of the shaft in a notionally optically non-transparent body.

Advantageously, the connection does not project laterally from the shadows, thereby requiring additional structural space.

A configuration of this type can be achieved in a particularly simple manner, if the connection is configured by way of a multilayer system, for example in the form of a multilayer printed circuit board. The flexible bending section can specifically be constituted as an uppermost layer of the multilayer system or of the multilayer printed circuit board.

Advantageously, this solution obviates any radial projection of the connection beyond the sensor such that, for a given sensor, the smallest possible endoscope cross-section can be achieved. For example, as by an arrangement of the above-mentioned type of the bending section of the connection, it can be achieved that the sensor, at its outer edges, engages with an interior wall of the shaft. In other words, using the invention, it can thus be achieved that an internal diameter of the shaft of the instrument, in the region of the sensor, is dictated by the sensor itself rather than, for example, by the connection. This results in a highly compact and miniaturized design of the instrument at the distal end of the shaft.

The contact-connection section can be variously configured, for example in the shape of an I, L, U, or H, depending upon the distribution of contacts on the reverse side of the sensor. The field on the reverse side preferably encompasses all the sensor contacts, wherein N contacts subtend the outline of the field, whereas further contacts can be arranged within the field.

Further advantageously, by use of the invention, space is provided for the arrangement of electrical and/or electronic components at the smallest possible distance from the sensor on the contact-connection section, in direct proximity to the sensor, as will be described in greater detail hereinafter. A peripheral auxiliary circuit of the sensor can thus be provided, with short signal paths.

As an alternative solution to a flat, i.e. a specifically planar contact-connection section, a contact-connection section is also conceivable, wherein the sensor contacts are contact-connected on the end face. This variant is specifically conceivable, if the contacts are configured within the field on the reverse side of the sensor in the form of a ball grid array. An end-face contact-connection of this type can be achieved, for example, by a circuit board which incorporates blanked and (vis-à-vis the circuit board plane) semi-open (for example, thus formed by saw-cutting) metal-plated passages in an end face. These semi-open metal-plated passages, which function in the manner of receiving sockets, can accommodate the individual contacts of the sensor. Electrical and mechanical connection between the passages and the contacts can then be achieved, for example, by soldering.

According to a further aspect of the present invention, potentially having an independently inventive character, in a multilayer system, a connection can be provided, preferably a connection, for example, by way of a connection according to the invention, specifically as described or claimed heretofore, wherein at least one electrical or electronic component, for example a resistor, a capacitor or an electronic chip, is at least partially arranged in one of the layers, preferably in an intermediate layer such as, for example, an insulating layer of the multi-layer system. To this end, the intermediate/insulating layer can incorporate a cut-out into which the component is inserted, specifically completely. As mentioned above, the multi-layer system can specifically be configured as a multilayer printed circuit board (multi-layer PCB).

For the manufacture of a compact connection of this type, with integrated components, the individual layers can firstly be structured and constituted, wherein, in one layer, a cut-out is incorporated, into which the component is inserted. Thereafter, the component which is inserted in the cut-out can be covered by the next layer. Thereafter, electrical contact-connection of the component can be achieved in a particularly simple manner, by the reflow method, which is known per se.

It is therefore particularly favorable, if the component is arranged in an inner layer of the multilayer system. In this case, contact-connection of the component from two sides is thus possible in a simple manner, i.e. from the upper and the underside, for example. It can thus be provided that the at least one component is covered by at least one further layer, specifically a conductive layer and/or a further insulating layer.

According to an alternative configuration, however, the cut-out in the multilayer system can also be configured in a semi-open manner, such that the component cannot be inserted into the cut-out until the system is assembled. This procedure is specifically appropriate for components having end-face and/or exposed-face contacts, which can then be electrically connected within the system by printed conductors, for example by the reflow method. A cut-out of this type can be formed by a production engineering method, for example by milling.

Additionally, the multilayer system can incorporate at least one passage which, however, is only partially filled with a soldering agent. In this case, an electrical conductor, for example a wire, can be introduced into the remaining unfilled space in the passage and connected with the solder material therein, such that a particularly robust electrical contact is constituted. Advantageously, a larger contact surface can be provided, as a soldered connection can not only be constituted on the end face, as in the case of a planar contact surface, but also on the circumferential sides of the wire section which is inserted in the passage. As a result, a particularly robust electrical contact-connection is achieved, which is also mechanically protected.

If the component is arranged in a cut-out, at least one channel can be routed to the cut-out from an upper side and/or from an underside. This channel, which can be employed for the electrical contact-connection of the component, can be lined with an electrically conductive material and/or can contain a soldering agent.

As mentioned above, this potentially independent concept can be employed in any multilayer system, wherein said concept can also be combined with the remaining characteristics and advantages from said description.

As the field defined by the contacts typically lies within a rear surface of the sensor, which frequently coincides with the cross-section of the sensor, but wherein the field does not occupy the entire rear surface, an interspace can remain between the inner wall of the shaft and the field, into which the connection can extend, with no resulting limitation, however, to the internal diameter of the shaft. A configuration of this type is then specifically advantageous, if the connection is electrically connected to the sensor by soldering. In this form of connection, a degree of tolerance is thus present in the relative positioning between the sensor and the connection, which can be accommodated by the provision of the interspace.

Thus, by use of a connection configured according to the invention, control signals and/or a current supply and/or a voltage supply can be reliably transmitted to the sensor, and/or signals can be derived from the sensor at the proximal end of the shaft. The sensor of the investigation instrument can be, for example, an image sensor, a temperature, pressure or humidity sensor or, for example, an ultrasound sensor. Naturally, the invention can also be employed for the connection of actuators such as, for example, micro-grippers or ultrasound transmitters which, in corresponding instruments, can be contact-connected in a similar manner to sensors by the invention. Additionally, an investigation instrument according to the invention can also incorporate lighting devices, such as LEDs, semiconductor lasers or similar, which can also be contact-connected on the reverse side by the connection as described above.

By use of the invention, it can specifically be achieved that the bending section and, optionally and preferably, even the entire connection lies within a rearward shadow which is cast by the sensor along the longitudinal axis. Accordingly, in the region of the sensor, the requisite internal diameter of the shaft, and thus the overall cross-section of the shaft, is only limited by the external dimensions of the sensor which, in the case of image sensors, corresponds to the footprint. The size, for example, of an endoscope at the distal end can thus be reduced in an optimum manner for any given image sensor.

According to the invention, the object can also be fulfilled by further advantageous embodiments, according to described below and in the claims.

For example, in the interests of a simple configuration of the connection, it is advantageous if a surface normal of the field is oriented at least approximately, or exactly parallel to the longitudinal axis of the shaft. Ideally, the contact-connection section is thus oriented at least approximately, or exactly parallel to the reverse side of the sensor. The sensor can thus be arranged at a distal end of the shaft, specifically oriented transversely to the longitudinal axis. In a sensor arrangement of this type, the bending section thus typically constitutes a diversion of the connection lines through approximately 90 degrees.

Alternatively or additionally, it can be provided that the surface normal of the field is oriented at an acute angle or an obtuse angle to the longitudinal axis of the shaft. An arrangement can thus be constituted in which the sensor is not arranged at right-angles to the longitudinal axis.

It can be provided that a viewing direction of the sensor is arranged at an angle α, which differs from zero, to a longitudinal axis, for example the above-mentioned longitudinal axis of the shaft.

In the interests of a particularly space-saving arrangement, it can be provided that the bending section is arranged within a shadow which is cast by the field along a longitudinal axis of the shaft (for example, the above-mentioned shadow), and within a shadow which is cast by the field along a rearward extension of a viewing direction of the sensor.

The present invention is applicable, in a particularly advantageous manner, to the configuration of optical endoscopes. The above-mentioned investigation instrument can thus specifically be an endoscope and the sensor can specifically be an image sensor. For example, in the event of the employment of a so-called "back-illuminated sensor" (BSI), i.e. an image sensor, the original chip underside of which, in the installed position, receives light, wherein electrical contacts are configured on the original upper side of the chip, contact-connection according to the invention might be achieved by the connection of the contact-connection section with the contacts of the original chip upper side of the BSI sensor. In such a case, the original chip upper side would thus correspond to the reverse side according to the invention.

According to a preferred configuration, the contacts can be configured on the reverse side of the sensor in the form of a ball grid array. This is understood as a geometrical arrangement of contacts which are configured on the reverse side of the sensor in the form of solder spheres. In a configuration of this type, the ball grid array can subtend the field. In a manner which is known per se, the ball grid array can be configured in a variety of polygonal arrangements, for example in the form of a square, a rectangle, a quadrilateral or a hexagon. It is preferred if a projection of the bending section along the longitudinal axis of the shaft on the reverse side of the sensor lies within the field or within said polygon.

The contact-connection section, depending upon the configuration of the field subtended by the contacts, can comprise either a complete or only a partial infill. Moreover, a projection of the bending section along the longitudinal axis can either fall between individual contacts, such that the bending section leads away the connection lines between the contacts, or said projection can coincide with individual contacts, in which case the bending section leads away the connection lines above the contacts. Additionally, these configurations can also be mutually combined, specifically if a plurality of bending or contact-connection sections are provided.

The contact-connection and bending sections of the connection can also be configured in multiple ways. For example, it can thus be provided that the connection comprises at least one flat contact-connection section and at least one flexible bending section. In the event of the employment of a plurality of contact-connection sections, each of the same can be individually contact-connected with the contacts within the field on the reverse side of the sensor. In the event of the employment of a plurality of bending sections, each of the same can respectively be arranged within the shadow which is cast by the field along the longitudinal axis of the shaft.

The connection can thus comprise a plurality of flexible bending sections, and specifically, additionally, a plurality of contact-connection sections. The bending sections can each lead out electrical connection lines from a respective contact-connection section of the connection. Preferably, each of the bending sections is arranged within a respective shadow which the respective contact-connection section casts along the longitudinal axis. The connection lines can be continued in the form of respective terminal sections, which are connected to the respective bending sections.

According to a further configuration, the connection thus comprises a terminal section, which leads the electrical connection lines further away from the sensor. The bending section connects the contact-connection section to the terminal section. A proximal dividing line can mark the transition from the bending section to the terminal section.

According to a preferred configuration, the terminal section carries and contact-connects at least one electrical component. It is further advantageous, if the terminal section is oriented along the longitudinal axis. In a configuration of this type, an extension of the terminal section can engage with the contact-connection section, and is thus arranged in the shadow thereof.

The terminal section(s) can be flexible and/or configured integrally with the respective bending section.

In one configuration of the invention, the connection is configured flexibly.

The connection as a whole can be of a one-part or multi-part construction, and is specifically configured as a printed circuit board, preferably having a plurality of conductor planes, by way of a multilayer printed circuit board. A procedure of this type fulfils the condition for an automated production and population of the connection, thereby reducing costs and, specifically, providing a basis for the employment of the connection, for example, in low-cost single-use endoscopes.

For a reliable connection of the sensor, it is preferred if the contact-connection section(s) is/are configured to a rigid design. The contact-connection section(s) can further be populated with electrical and/or electronic components on the reverse side. In general, it is advantageous if the contact-connection section(s) is/are configured with a smaller footprint than the sensor.

According to a preferred variant, the respective bending section, and preferably also the respective terminal section and/or the respective contact-connection section, is at least partially formed of a polyimide film. In this case, the connection, whether in whole or in part, and thus specifically the bending section and, preferably, also the respective terminal section, can be produced by wafer-level processes.

By way of distinction from many previously known concepts, by the configuration of the instrument according to the invention, the bending section of the connection can be configured with a large bending radius, with no associated sacrifice of structural space. Consequently, the radius of curvature of the bending section can be specifically greater, for example, than one third of the edge length of the field on the reverse side of the sensor. The edge length can preferably lie in the plane of the radius of curvature, specifically with respect to a desired installation position.

The transition from the contact-connection section to the bending section can be marked by a distal dividing line. In specific configurations of the invention, this distal dividing line is routed in at least one, but preferably in both of its potential extensions within the contact-connection section. The bending section can thus be arranged, for example, laterally at the edge of the field, or else in the center of the field.

According to a further potential configuration, the proximal dividing line, and preferably also the distal dividing line lie directly outside a shadow which is cast by the contact-connection section along the longitudinal axis. In such a configuration, wherein the contact-connection section, in general, only partially covers the field of the contacts, the bending section thus assumes only a partial overlap, or no overlap at all with the contact-connection section, in a projection along the longitudinal axis. Specifically in a complete absence of an overlap, the contact-connection section and the bending section can be formed of a flexible layer, for example a polyimide film, wherein additional reinforcements can be provided in the region of the contact-connection section.

In other further configurations, a projection of the proximal dividing line and/or of the bending section, along the longitudinal axis in each case, at least partially coincides with the contact-connection section. In this case, there is thus a partial, or even a full overlap between the bending section and the contact-connection section, if the connection is considered in the installation position along the longitudinal axis. A configuration of this type can be advantageous for sensors which comprise a large number of electrical contacts, such that the field can be virtually entirely occupied by contacts.

Finally, in the interests of a simple assembly of the investigation instrument, it can be advantageous if the terminal section(s) is/are configured to a length-variable design. This can be achieved, for example, wherein the terminal section(s) is/are configured in a meander shape or a spiral shape.

BRIEF DESCRIPTION OF THE DRAWINGS

The invention will now be described in greater detail with reference to exemplary embodiments, but is not limited to these exemplary embodiments.

Further exemplary embodiments proceed from a mutual combination of the characteristics of individual or multiple claims for protection and/or from the combination thereof with individual or multiple characteristics of the respective exemplary embodiment. Specifically, configurations of the invention can thus be inferred from the following description of a preferred exemplary embodiment in conjunction with the general description, the claims and the drawings.

In the drawings:

Figure 1:
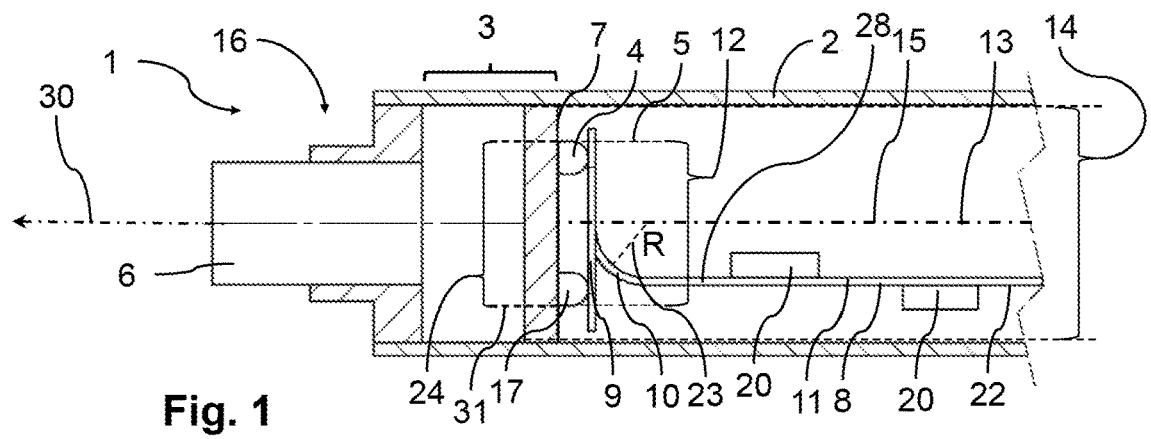
Figure 2:
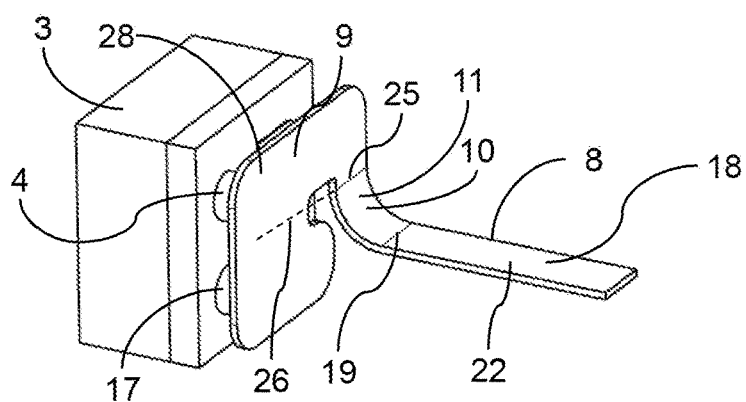
Figure 3:
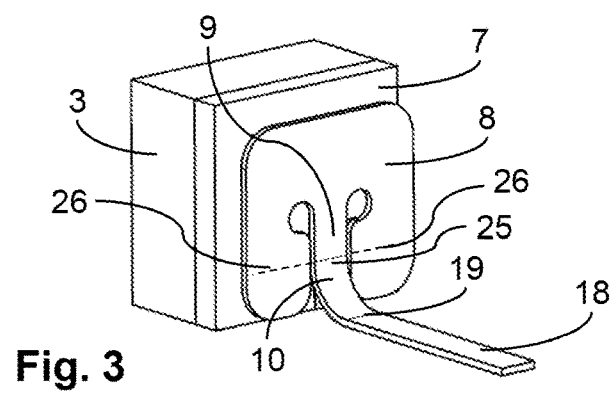
Figure 4:
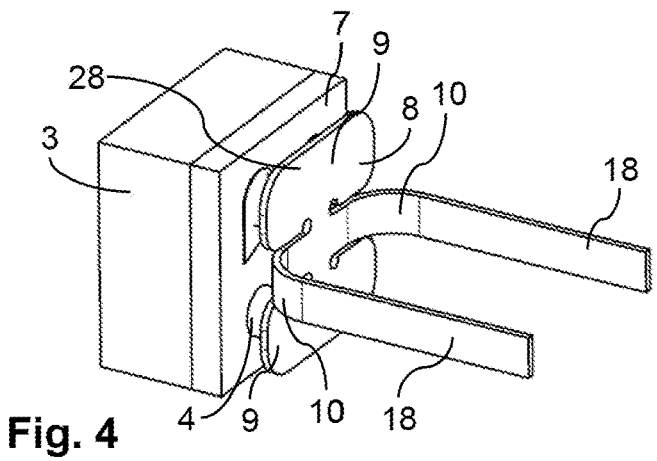
Figure 5:
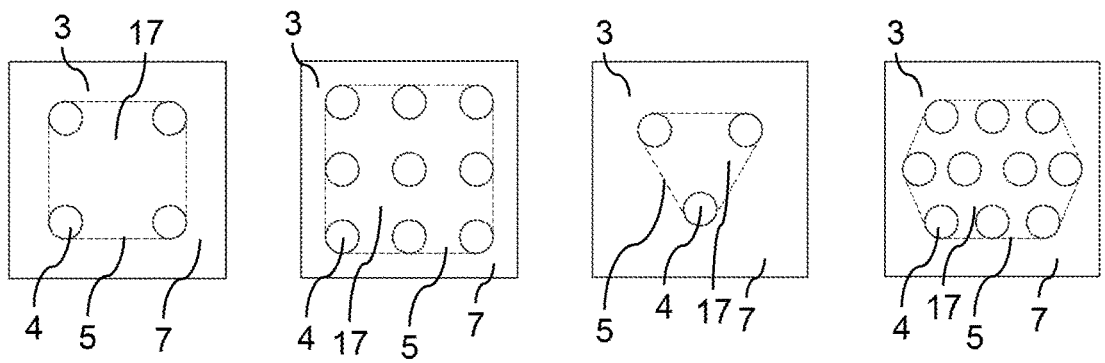
Figure 6:
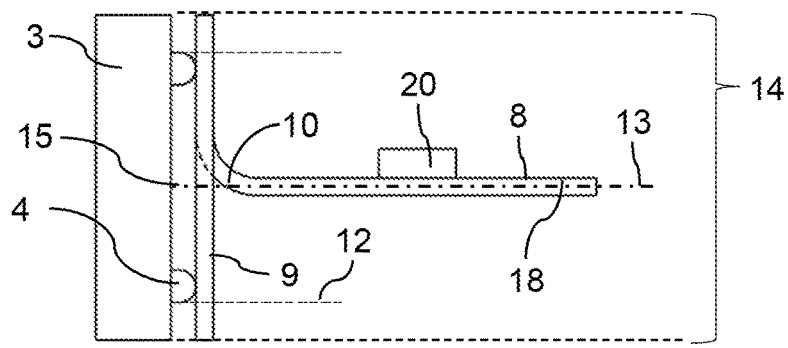
Figure 7:
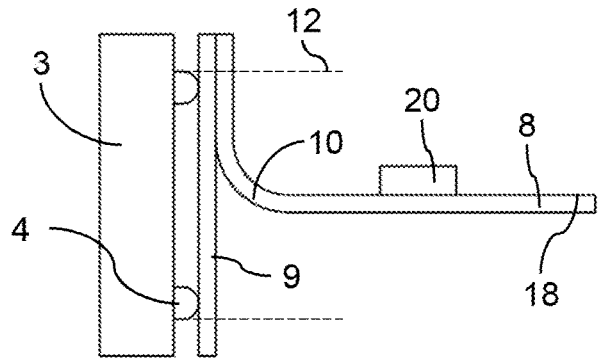
Figure 8:
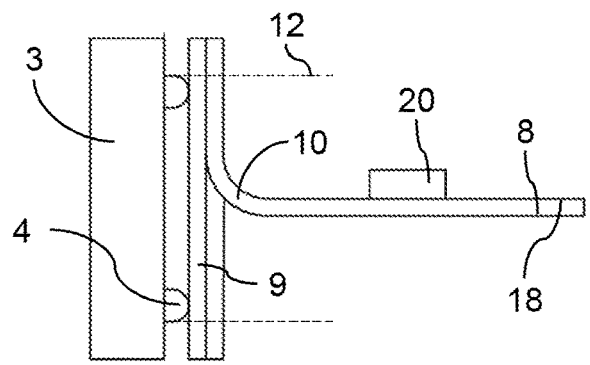
Figure 9:
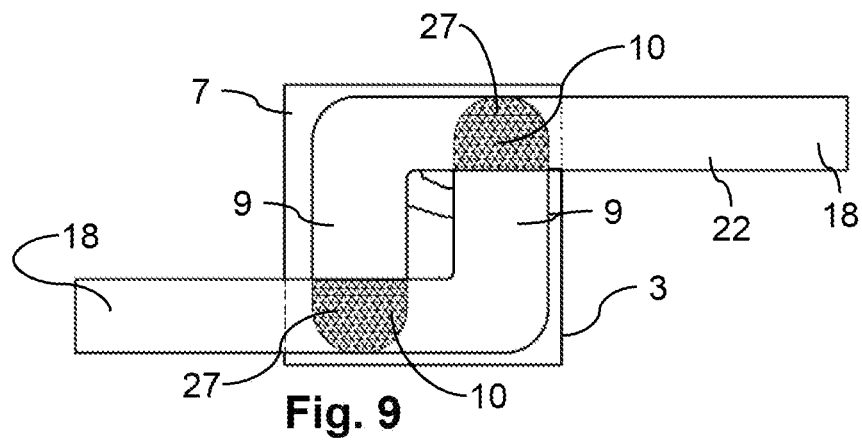
Figure 10:
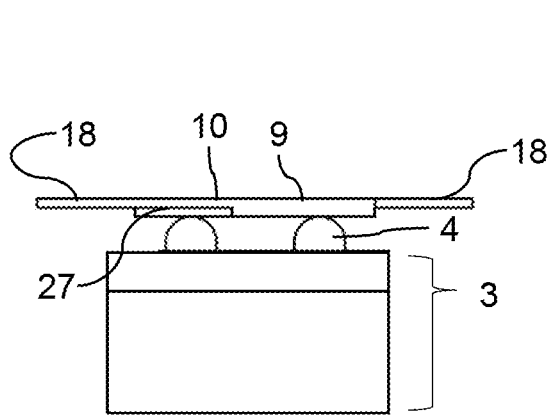
Figure 11:
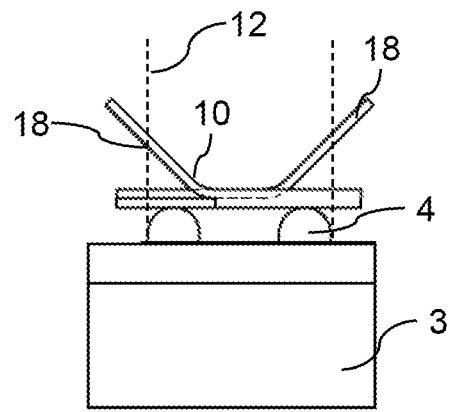
Figure 12:
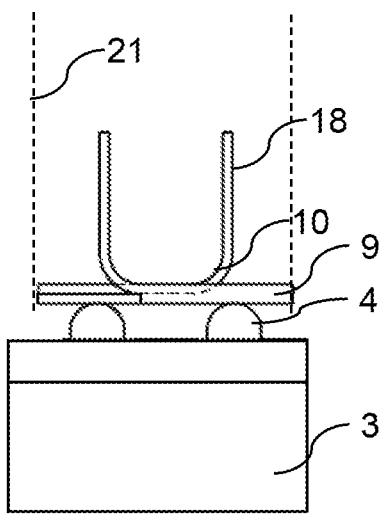
Figure 13:
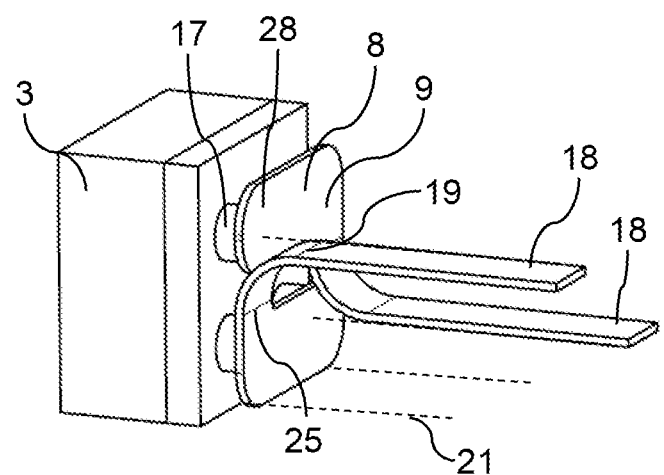
Figure 14:
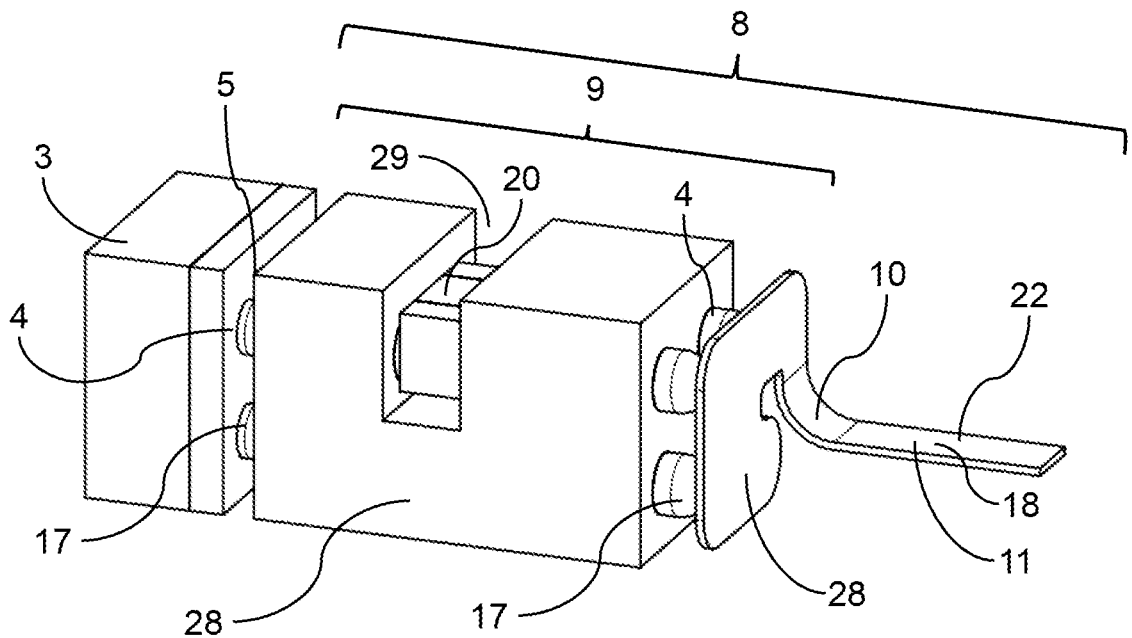
Figure 15:
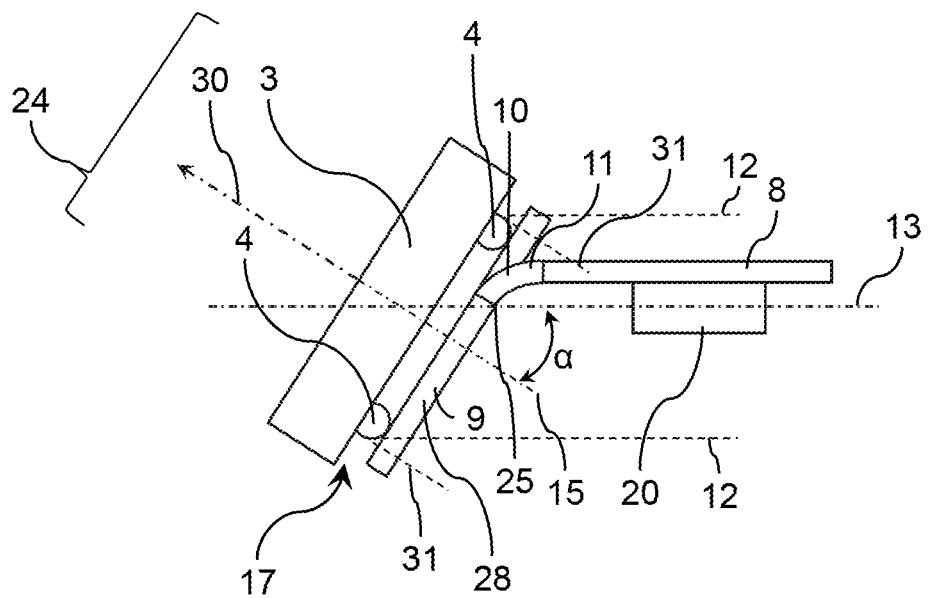

FIG. 1 shows a longitudinal section of an investigation instrument according to the invention, in the form of an optical endoscope, FIG. 2 shows a detailed perspective view of a potential contact-connection of an image sensor of the endoscope according to FIG. 1, by a connection which is configured according to the invention, FIG. 3 shows a further potential configuration of a connection for the electrical connection of the image sensor of the endoscope according to FIG. 1, FIG. 4 shows another further potential configuration of a connection for the electrical connection of the image sensor of the endoscope according to FIG. 1, FIG. 5 shows various views of the reverse side of the image sensor of the endoscope according to FIG. 1, FIG. 6 shows a side view of the connection according to the invention represented in FIG. 2, with the sensor connected thereto, FIG. 7 shows a side view of a further potential configuration of a connection according to the invention, FIG. 8 shows a side view of another further potential configuration of a connection according to the invention, FIG. 9 shows an overhead view of the reverse side of a sensor, by which a connection according to the invention is contact-connected, FIG. 10 shows a side view of the connection illustrated in FIG. 9, FIG. 11 shows the same view as FIG. 10, but after the bending up of the bending sections of the connection, FIG. 12 shows the same view as FIG. 11, after the full alignment of the bending sections, FIG. 13 shows the connection from FIGS. 9 to 12 in its final arrangement for the contact-connection of the image sensor of the endoscope according to FIG. 1, FIG. 14 shows a further potential configuration of a connection according to the invention, and FIG. 15 shows a further potential configuration of a connection according to the invention, with an image sensor arranged at an angle to the longitudinal axis of the shaft.

DETAILED DESCRIPTION

In the following description of various forms of embodiment of the invention, elements which coincide in their function, but which differ in design or shape, are identified by matching reference numbers.

FIG. 1 shows a simplified cross-sectional representation of an investigation instrument, identified overall by the number 1, in the form of an optical endoscope having an image sensor 3 which is arranged at the distal end 16 of a shaft 2 of the endoscope, and which receives light at its front side through an optical assembly 6. On its reverse side 7, the sensor 3 comprises a plurality of contacts 4 in the form of a ball grid array 17, as represented on the far left of FIG. 5. The contacts 4 subtend a field 5 on the reverse side 7 of the sensor 3, which is also represented in the illustration on the far left of FIG. 5.

The sensor 3 in FIG. 1 is electrically contact-connected by a connection which is configured according to the invention, identified by the number 8. To this end, the connection 8 comprises a flat contact-connection section 9 which contact-connects the contacts 4, wherein, to this end, metallic soldering surfaces on the underside of the contact-connection section 9 are soldered to the contacts 4 of the ball grid array 17, which are individually configured as solder spheres. From the contact-connection section 9, a flexible bending section 10 leads out electrical connection lines 11 to the rear of the sensor 3, wherein each of the connection lines 11 is electrically connected with one of the contacts 4. As can clearly be seen in FIG. 2, the bending section 10, at a proximal dividing line 19, forms a transition to a terminal section 18 of the connection 8, wherein the transition from the contact-connection section 9 to the bending section 10 is marked in FIG. 2 by a distal dividing line 25.

The overall connection 8 is configured in the form of a multilayer printed circuit board 28 (multilayer PCB), wherein the contact-connection section 9 is configured rigidly, and the bending section 10 is configured flexibly. Depending upon specific requirements, manifold configurations of the connection 8 are possible, as specifically illustrated in FIGS. 2 to 4 and 6 to 8.

As can clearly be seen from the broken lines in FIG. 1, identified by reference number 12, the bending section 10 lies within a notional shadow 12 cast by the field 5 on the reverse side 7 of the sensor 3 along the longitudinal axis 13 of the shaft 2 of the endoscope. This shadow 12 corresponds to the volume generated by the projection of the virtually quadratic field 5 represented on the far left of FIG. 5 along the longitudinal axis 13.

A rearward shadow 14 of this type can also be assigned to the sensor 3 of the endoscope, wherein the marginal rays of the shadow 14 are oriented directly along the inner wall of the shaft 2, given that the sensor 3, as can be seen in FIG. 1, engages with the inner wall of the shaft 2, and thus defines the minimum internal diameter of the shaft 2 in the region of the image sensor 3. As illustrated in FIG. 1 by further broken lines, both the bending section 10 and the entire connection 8 lie within this shadow 14.

It is moreover evident that the surface normal 15 of the field 5, and that of the frontal sensor surface of the image sensor 3, are oriented parallel to the longitudinal axis 13, such that the image sensor 3 assumes a frontward viewing direction along the longitudinal axis 13. Conversely, the contact-connection section 9 is arranged with a 90-degree rotation vis-à-vis the longitudinal axis, and is thus oriented parallel to the reverse side 7 of the sensor 3. The arrangement of the sensor 3 can thus be described as transverse to the longitudinal axis 13 of the endoscope. On the grounds of this arrangement, it is advantageous if a longitudinal section of the bending section 10 describes exactly one quarter-circle, as is the case, for example, in FIG. 1 and FIG. 2.

In the cross-section of FIG. 1, it can further be clearly seen that a non-occupied interspace is present between the inner wall of the shaft 2 and the connection 8, specifically in the region of the contact-connection section 9, but also in the region of the terminal section 18. This is possible on the grounds that the field 5, as can also be clearly seen on the far left of FIG. 5, does not occupy the entire reverse side 7 of the sensor 3, and a clearance thus remains between the outermost of the contacts 4 and the outer edge of the sensor 3. Consequently, the contact-connection section 9 does not engage with the inner wall of the shaft 2, even though the contact-connection section 9 projects slightly beyond the field 5, as indicated in FIG. 1 by the broken lines, identified by reference number 12, as the contact-connection section is configured with a smaller surface area than the footprint of the sensor 3.

The interspace is moreover employed for the arrangement of electronic components 20 on the upper side and underside of the terminal section 18, and for contact-connection thereto, as illustrated in FIG. 1, wherein additionally—although not represented in FIG. 1—further components 20 can be arranged and contact-connected on the reverse side of the contact-connection section 9, which is averted from the sensor 3.

It can only be inferred from FIG. 1 that a projection of the bending section 10 along the longitudinal axis 13 on the reverse side of the sensor 7 lies within the field 5. In other words, the electrical connection lines 11 are thus led away by the bending section 10 within the field 5, proximally in relation to the instrument 1.

FIGS. 2 to 4 represent further potential configurations of connection 8 according to the invention, which respectively execute the contact-connection of the sensor 3 of the endoscope according to FIG. 1. In the examples according to FIGS. 2 and 3, one contact-connection section 9 respectively and one bending section 10 respectively are constituted whereas, in the example according to FIG. 4, the connection 8 comprises two mutually connected contact-connection sections 9, wherein two bending sections 10 lead out the connection lines 11, which are electrically connected to the contacts 4 of the sensor 3, in the proximal direction, and respectively form a transition to two terminal sections 18.

In FIGS. 3 and 4, the contact-connection sections 9 respectively occupy only a part of the field 5, which is subtended by the contacts 4 of the sensor 3. In the remaining part of the field 5, for example in the central strip in FIG. 3, the respective bending sections 10 are arranged. The projection of the respective bending section 10 along the longitudinal axis 13 thus falls between the contacts 4 of the sensor 3, as can specifically be clearly seen in FIG. 4, as both contact-connection sections 9 are contact-connected with all the contacts 4 of the field 5. In the configurations according to FIGS. 3 and 4 there is thus no overlap between the bending section 10 and the respective contact-connection section 9.

In the embodiment represented in FIG. 2, conversely, the bending section 10 leads out the electrical connection lines partially above the contacts 4 (considered from the longitudinal axis 13), as the projection of the bending section along the longitudinal axis 13, in this case, at least partially coincides with the lower right-hand contact 4 of the sensor 3 represented in FIG. 2 (c.f. additionally the illustration on the far left of FIG. 5, from which the position of the lower right-hand contact 4 can be seen). It can further be seen that, in the example represented in FIG. 2, an extension of the terminal section 18 along the longitudinal axis 13 would engage with the contact-connection section 9.

From the consideration of the notional shadows in FIGS. 3 and 4 respectively, which are cast by the respective contact-connection section 9 along the longitudinal axis 13, it proceeds that both the proximal dividing line 19 and the distal dividing line 25 lie directly outside this shadow.

In the exemplary embodiment represented in FIG. 2, conversely, the projection of the proximal dividing line 19 entirely, and that of the bending section 10 at least partially engages with the contact-connection section 9 such that, in this case, a complete or partial overlap can be described.

An overlap of this type also exists in a further exemplary embodiment, which is represented in FIGS. 9 to 13: from this sequence of images, it can clearly be seen how the originally flattened terminal sections 18 are respectively oriented along the longitudinal axis 13, wherein the bending sections 10 are bent up (c.f. FIG. 11) to the extent that they assume the final curvature illustrated in FIG. 13.

From the broken lines in FIG. 13, it can clearly be seen that, in the final installation position, the notional extensions of the terminal sections 18, in the distal direction, and the projections of the bending sections 10 engage with the respectively adjoining contact-connection sections 9. In relation to the contact-connection section 9, from which the respective bending section 10 originates, however, the proximal dividing line 19 and the distal dividing line 25 lie directly outside the shadow 21 which is cast by said contact-connection section 9 along the longitudinal axis 13. An arrangement of the type represented in FIG. 13 permits an extremely compact design and, simultaneously, a reliable derivation of signals from the sensor 3.

In order to facilitate the release and the upward bending of the bending sections 10, and to permit the prevention of short-circuits, as represented in FIG. 9, passivated regions 27 are provided between the contact-connection sections 9 and the bending sections 10.

The connection 8 represented in FIG. 1 is configured as a multi-layer printed circuit board of a one-piece flexible polyimide film 22, wherein, in the region of the contact-connection section 9, reinforcements are provided for the rigid configuration of said section. The bending section 10 and the terminal section 18, conversely, are flexibly configured.

Additionally, hybrid concepts can be applied, as illustrated in FIG. 7, wherein the contact-connection section 9 is configured as a rigid circuit board with a flexible bending section 10 applied thereto, and a flexible or rigid terminal section 18 connected thereto. In this example, the connection 8 is thus constituted of different components.

Another further option is illustrated in FIG. 8. Here again, a rigid circuit board is employed as a contact-connection 9. However, this circuit board comprises a plurality of layers, wherein the uppermost level is configured flexibly, and both the bending section 10 and the terminal section 18 are formed from this upper layer of the circuit board.

In all the examples in FIGS. 6 to 8, it will be seen, however, that the bending section 10 is respectively arranged within the shadow 12 which is cast by the field 5 along the longitudinal axis 13. The field itself 5, in turn, can assume manifold polygonal shapes, as can be seen with reference to the various configurations of ball grid arrays 17, which are represented in FIG. 5.

From a comparison of the radius of curvature 23 of the bending section 10 identified in FIG. 1 by the reference symbol R, it is clear that this is greater than one third of the edge length 24 of the field 5, measured in the plane of the radius of curvature 23 represented in FIG. 1.

The distal dividing line 25 and the proximal dividing line 19 illustrated in FIG. 2, but also in FIGS. 3 and 4, have already been described. In FIG. 2, it can be seen that the extension of the distal dividing line 25, identified by reference number 26, only engages with the contact-connection section 9 on one side, whereas the corresponding extension 26 in FIG. 3 engages with the contact-connection section 9 on both sides of the distal dividing line 25. The invention can thus be executed by laterally arranged bending sections 10, as illustrated in FIG. 2, or by centrally arranged (in each case, with respect to the field 5) bending sections 10, as illustrated in FIGS. 3 and 4.

Finally, FIG. 14 shows a further potential configuration of a connection 8 according to the invention. The contact-connection section 9, which contact-connects the electrical contacts 4 of the sensor 3, is configured as a rigid multi-layer printed circuit board 28. The multilayer printed circuit board 28 incorporates a cut-out 29, into which an electrical component 20 is inserted. The electrical component 20 is thus arranged in one of the layers of the multilayer printed circuit board 28.

As can clearly be seen in FIG. 14, the electrical component 20 is electrically contact-connected at its end face by an intermediate layer of the multi-layer printed circuit board 28. At its end face, the multilayer printed circuit board 28, in turn, by a flat side wall, contact-connects the reverse-side contacts 4 of the sensor 3, which are configured in the form of a ball grid array.

On an end face of the multilayer printed circuit board 28, which is averted from the sensor 3, further contacts 4 are configured. These are contact-connected by a further multilayer printed circuit board 28, which also incorporates a flexible bending section 10.

Thus, in the exemplary embodiment represented in FIG. 14, a connection 8 is constituted by the electrical coupling of a rigid first multilayer printed circuit board 28 (shown centrally in FIG. 14) with a partially flexibly configured second multilayer printed circuit board 28 (shown on the right-hand side of FIG. 14). The latter also comprises a terminal section 18, the function of which is to relay electrical signals from the sensor 3 along and within a shaft of an investigation instrument 1. Again, in this configuration, the bending section 10 lies within the shadow 12 which is cast by the field 5, which is subtended by the contacts 4 of the sensor 3, along a longitudinal axis 13 of the shaft 2. As can clearly be seen, the entire arrangement, comprised of the sensor 3 and the connection 8, transversely to the shaft direction, is only dictated by the (requisite) external dimensions of the sensor 3. Accordingly, this arrangement also permits the achievement of the most compact possible design of the investigation instrument 1, in the lateral direction.

FIG. 15 shows a further exemplary embodiment of an investigation instrument according to the invention. Details of the investigation instrument, which are not required for the clarification of the difference vis-à-vis the preceding exemplary embodiments, have been omitted in the interests of clarity. Details which, structurally and/or functionally, correspond to components and functional units of the preceding exemplary embodiments, are identified by the same reference symbols, and are not described again in a separate manner. Comments with respect to FIGS. 1-14 therefore apply correspondingly to FIG. 15.

The exemplary embodiment according to FIG. 15 differs from the preceding exemplary embodiments, in that the sensor 3 assumes a viewing direction 30 which is inclined by an angle α in relation to the longitudinal axis 13 of the shaft 2.

Accordingly, the shadow which is formed by a rearward extension 31 of the viewing direction 30, and the shadow 12 which is formed by an extension along the longitudinal axis 13 of the shaft 2, do not coincide. However, the bending section 10 is included in both shadows.

This permits a space-saving arrangement of the connection 8, even in the event of an inclined sensor 3, wherein the connection 8 likewise requires no additional lateral structural space.

In summary, for the miniaturization of an investigation instrument 1, which comprises a sensor 3, which is arranged in the interior of a long shaft 2 and is electrically contact-connected by a connection 8, it is provided that a flexible bending section 10 is configured on the connection 8, and is thus connected with a contact-connection section 9, which is contact-connected with contacts 4 of the sensor 3 on the reverse side such that, firstly, the entire connection 8 is arranged in the shadow of the image sensor 3 and, secondly, the bending section 10 originates from the contact-connection section 9 within a field 5 which is subtended by the reverse-side contacts 4 of the sensor 3.

LIST OF REFERENCE NUMBERS

1 Investigation instrument
2 Shaft
3 Sensor (e.g. image sensor)
4 Electrical contact
5 Field
6 Optical assembly
7 Reverse side (of 3)
8 Connection
9 Contact-connection section (of 8)
10 Bending section (of 8)
11 Connection lines
12 Shadow (of 5)
13 Longitudinal axis (of 2)
14 Shadow (of 3)
15 Surface normal (of 5)
16 Distal end (of 2)
17 Ball grid array (BGA)
18 Terminal section
19 Proximal dividing line
20 Electrical/electronic component
21 Shadow (of 9)
22 Polyimide film
23 Radius of curvature (of 10)
24 Edge length (of 5)
25 Distal dividing line
26 Extension (of 25)
27 Passivated region 28 Multilayer printed circuit board (multilayer PCB)
29 Cut-out
30 Viewing direction
31 Rearward extension in the viewing direction

The invention claimed is:
1. An investigation instrument (1) comprising:
a shaft (2),
a sensor (3) arranged in the shaft, the sensor including reverse-side electrical contacts (4) which subtend a field (5) on a reverse side (7) of the sensor (3), by which the sensor is electrically contact-connected by a connection (8),
the connection (8) comprises a flat contact-connection section (9) in direct planar contact with each of the electrical contacts (4) of the sensor, at least one flexible bending section (10) having a radius of curvature (23) that is greater than one third of an edge length (24) of the field (5) and the edge length (24) lies in a plane of the radius of curvature (23), the at least one flexible bending section (10) including a respective electrical connection line (11) brought out from the flat contact-connection section (9) at the reverse side (7) of the sensor (3) to a respective terminal section (18) of the connection (8), each of the at least one flexible bending section (10) is arranged within a shadow (12) which is cast by the field (5) subtended by the contacts (4) along at least one of a longitudinal axis (13) of the shaft (2) or along a rearward extension (31) of a viewing direction (30), and the respective terminal section (18) is connected to the flat contact-connection section (9) by only a single one of the at least one flexible bending section (10), and
each of the at least one flexible bending section (10) located within said shadow (12) starts out from the flat contact-connection section (9) and terminates in the respective terminal section (18).

2. The investigation instrument (1) as claimed in claim 1, wherein the at least one flexible bending section (10) lies within a rearward shadow (14), which is cast by the sensor (3) along the longitudinal axis (13).

3. The investigation instrument (1) as claimed in claim 1, wherein a surface normal (15) of the field (5) is oriented at least approximately parallel, or at an acute or obtuse angle to the longitudinal axis (13), and the contact-connection section (9) is oriented at least approximately parallel to the reverse side (7) of the sensor (3).

4. The investigation instrument (1) as claimed in claim 1, wherein the sensor (3) is arranged at a distal end (16) of the shaft (2), transversely to the longitudinal axis (13).

5. The investigation instrument (1) as claimed in claim 1, wherein a viewing direction (30) of the sensor (3) is arranged at an angle (a), which differs from zero, to the longitudinal axis (13) of the shaft (2), and the at least one flexible bending section (10) is arranged within the shadow (12) which the field (5) casts along the longitudinal axis (13) of the shaft (2), and is arranged within a shadow which the field (5) casts along a rearward extension (31) of a viewing direction (30) of the sensor (3).

6. The investigation instrument (1) as claimed in claim 1, wherein the investigation instrument (1) comprises an endoscope and the sensor (3) is an image sensor.

7. The investigation instrument (1) as claimed in claim 1, wherein the contacts (4) are configured as a ball grid array (17), and the ball grid array (17) subtends the field (5).

8. The investigation instrument (1) as claimed in claim 7, wherein a projection of the at least one flexible bending section (10) along the longitudinal axis (13) on the reverse side of the sensor (3) lies within the field (5).

9. The investigation instrument (1) as claimed in claim 1, wherein the contact-connection section (9) only partially occupies the field (5), and a projection of the first flexible bending section (10) along the longitudinal axis (13) either falls between individual ones of the contacts (4) or coincides with individual contacts (4), such that the at least one flexible bending section (10) leads away the connection lines (11) either between the contacts (4) or above the contacts (4).

10. The investigation instrument (1) as claimed in claim 1, wherein a proximal dividing line (19) marks a transition from the bending section (10) to the terminal section (18), and the terminal section (18) carries and contact-connects at least one electrical component (20).

11. The investigation instrument (1) as claimed in claim 10, wherein the terminal section (18) is oriented along the longitudinal axis (13) and an extension of the terminal section (18) engages with the contact-connection section (9).

12. The investigation instrument (1) as claimed in claim 1, wherein the connection (8) comprises a plurality of the contact-connection sections (9), a plurality of the flexible bending sections (10), the flexible bending sections (10) each lead out ones of the electrical connection lines (11) from respective ones of the contact-connection sections (9) of the connection (8), and each of the flexible bending sections (10) is arranged within a respective shadow (21) which is cast by the respective contact-connection section (9) along the longitudinal axis (13), and the connection lines (11) are continued in the form as respective ones of the terminal sections (18), which are connected to the respective bending sections (10).

13. The investigation instrument (1) as claimed in claim 1, wherein the connection (8) is configured as a multilayer printed circuit board having a plurality of conductor planes, the contact-connection section (9) is at least one of rigidly configured, populated on a reverse side with electrical components (20), or configured with a smaller footprint than the sensor (3), or wherein the terminal section (18) is at least one of flexibly configured or integrally configured with the respective first flexible bending section (10).

14. The investigation instrument (1) as claimed in claim 12, wherein the respective flexible bending section (10), and the respective terminal section (18), is formed of a polyimide film (22).

15. The investigation instrument (1) as claimed in claim 1, wherein a distal dividing line (25), which marks a transition from the contact-connection section (9) to the bending section (10), in at least one extension (26), is routed within the contact-connection section (9).

16. The investigation instrument (1) as claimed in claim 10, wherein the proximal dividing line (19) lies directly outside a shadow (21) which is cast by the contact-connection section (9) along the longitudinal axis (13), or wherein a projection of at least one of the proximal dividing line (19) or of the at least one flexible bending section (10) along the longitudinal axis (13) at least partially coincides with the contact connection section (9).

17. The investigation instrument (1) as claimed in claim 1, wherein the terminal section (18) is configured with a length-variable design having at least one of a meander shape or a spiral shape.

18. The investigation instrument (1) as claimed in claim 1, wherein all of the flexible bending sections (10) of the connection (8) in vicinity to the sensor (3) are arranged within the shadow (12).

19. An investigation instrument (1) comprising:

a shaft (2), a sensor (3) arranged in the shaft, the sensor including reverse-side electrical contacts (4) which subtend a field (5) on a reverse side (7) of the sensor (3), by which the sensor is electrically contact-connected by a connection (8), the connection (8) comprises a flat contact-connection section (9) in direct contact with the electrical contacts (4) of the sensor, at least one flexible bending section (10) having a radius of curvature (23) that is greater than one third of an edge length (24) of the field (5) and the edge length (24) lies in a plane of the radius of curvature (23), the at least one flexible bending section (10) including a respective electrical connection line (11) brought out from the flat contact-connection section (9) at the reverse side (7) of the sensor (3) to a respective terminal section (18) of the connection (8), each of the at least one flexible bending section (10) is arranged within a shadow (12) which is cast by the field (5) subtended by the contacts (4) along at least one of a longitudinal axis (13) of the shaft (2) or along a rearward extension (31) of a viewing direction (30), and the respective terminal section (18) is connected to the flat contact-connection section (9) by only a single one of the at least one flexible bending section (10), and each of the at least one flexible bending section (10) located within said shadow (12) starts out from the flat contact-connection section (9) and terminates in the respective terminal section (18).

\* \* \* \* \*